(12) United States Patent
Ikeda et al.

(10) Patent No.: US 6,608,309 B2
(45) Date of Patent: Aug. 19, 2003

(54) METHOD FOR MEASURING CONCENTRATION OF TRACE AMOUNT OF OH-GROUPS CONTAINED IN QUARTZ GLASS

(75) Inventors: Toru Ikeda, Koriyama (JP); Yasushi Fukui, Sasebo (JP); Tomomitsu Yaginuma, Koriyama (JP); Hidenori Ochiai, Koriyama (JP); Oliver Humbach, Alzenau-Michelbach (DE); Ralph Sattmann, Aschaffenburg (DE)

(73) Assignees: Heraeus Tenevo AG, Hanau (DE); Shin-Etsu Quartz Products Co., Ltd., Tokyo (JP)

( * ) Notice: Subject to any disclaimer, the term of this patent is extended or adjusted under 35 U.S.C. 154(b) by 0 days.

(21) Appl. No.: 09/844,119

(22) Filed: Apr. 27, 2001

(65) Prior Publication Data
US 2002/0096636 A1 Jul. 25, 2002

(30) Foreign Application Priority Data

May 1, 2000 (JP) ........................................ 2000-132774
May 1, 2000 (JP) ........................................ 2000-132778

(51) Int. Cl.[7] .................................................. G01J 5/02
(52) U.S. Cl. .............................. 250/339.06; 250/339.01
(58) Field of Search ...................... 250/339.06, 339.01; 501/54; 356/419, 326, 416

(56) References Cited

U.S. PATENT DOCUMENTS

| | | | | |
|---|---|---|---|---|
| 5,364,433 A | * | 11/1994 | Nishimura et al. | 65/17.4 |
| 5,424,545 A | * | 6/1995 | Block et al. | 250/343 |
| 5,837,334 A | * | 11/1998 | Yokokawa et al. | 428/34.4 |
| 2002/0038557 A1 | * | 4/2002 | Matsuo et al. | 65/17.4 |

OTHER PUBLICATIONS

Agarwal, et al, "A Simple IR Spectroscopic Method for Detemining Fictive Temperature of Silica Glasses", Journal of Non–Crystalline Solids, 185 (1995), 191–198.

* cited by examiner

Primary Examiner—David Porta
Assistant Examiner—Christine Sung
(74) Attorney, Agent, or Firm—Milde & Hoffberg, LLP

(57) ABSTRACT

A method for measuring trace quantities of OH groups in quartz glass comprises preparing a set of test pieces comprising a reference test piece from a blank of a quartz glass body whose OH group content is known and a sample test piece from a quartz glass body whose OH group content is to be measured, having two planar planes faced to each other, setting the sample test piece and the reference test piece in an infrared spectrophotometer; successively irradiating perpendicular to one of the two planar planes an incident infrared radiation in a wavelength region of approximately 2500 nm to approximately 2950 nm, while simultaneously detecting the outgoing radiation spectrum from the other plane; obtaining the difference of the outgoing radiation spectrum of each of the test pieces; selecting the absorbance peak assigned to OH groups at a wavelength of 2720 nm to obtain the peak height thereof; and calculating the concentration of OH groups from the peak height in the sample test piece.

11 Claims, 4 Drawing Sheets

METHOD FOR MEASURING CONCENTRATION OF TRACE AMOUNT OF OH-GROUPS CONTAINED IN QUARTZ GLASS

FIELD OF THE INVENTION

The present invention relates to a method for measuring the concentration of trace amounts of OH groups that are contained in quartz glass, especially in quartz glass to be used in preforms of optical fibers, cells for use in spectroscopy and lamps.

In particular the invention relates to a method for measuring a low concentration of OH groups (less than 1 ppm) at high precision.

BACKGROUND OF THE INVENTION

Much attention is paid on the content of OH groups that are incorporated in quartz glass, for instance, in optical fibers, because OH groups increase the transmission loss of light. Conventionally, an infrared spectrophotometer has been used to measure the concentration of the OH groups contained in quartz glass, and by measuring the height of the absorbance peak in the near infrared region attributed to the OH groups, the concentration is calculated in accordance with the following equation:

$$C_{sample} = \Delta A / L \times (M_H + M_O) / \varrho \times 10^3 \qquad (1),$$

wherein $C_{sample}$ represents the concentration of OH groups that are present in the sample test piece (in wt·ppm); $\Delta A$ represents the peak height (ABS); L represents the length (cm) of optical path; $\epsilon$ represents the absorption coefficient ($1 \cdot mol^{-1} \cdot cm^{-1}$), $M_H$ represents the atomic weight of hydrogen; $M_O$ represents the atomic weight of oxygen; and $\varrho$ represents the density ($g \cdot cm^{-3}$) of quartz glass.

However, in the measuring method above, the intensity of the absorbance peak decreases with decreasing concentration of OH groups making the accurate measurement of the concentration difficult. Thus, even if the absorbance peak having the highest sensitivity at a wavelength of 2720 nm is used, the detection limit of the concentration for an optical path length of 1 cm is said to be about 1 ppm. Accordingly, since the height of the absorbance peak increases in proportion to the length of optical path, it has been proposed to make the optical path longer, but a longer optical path length results in an increase in absorbance for the longer wavelength side due to the increase in base absorption of the quartz glass. This led to a loss in measurement precision due to the baseline inclining upward with increasing wavelength. Although it is possible to circumvent the interference of this base absorption by selecting the absorbance peak at a wavelength of 1380 nm attributed to OH groups, it was still unfeasible to perform measurements with high precision if a conventional test specimen was used, because the sensitivity was lowered to about $\frac{1}{160}$. In the light of such circumstances, the concentration of OH groups that are present in trace quantity in quartz glass has been determined by preparing optical fibers of the quartz glass, and by then selecting the less sensitive absorbance peak at a wavelength of 1380 nm by taking advantage of the superior light transmission characteristics and the increase in optical path length.

However, in the conventional method described above, the measurement was made possible only after the quartz glass is drawn into an optical fiber, and it was impossible to determine the concentration of the OH groups that are incorporated in trace quantities in the preforms. Furthermore, it was not feasible to measure the concentration of the OH groups contained in the quartz glass that are used in applications other than optical fibers such as the cells for use in spectroscopy, quartz glass tubes for lamps, etc.

SUMMARY OF THE INVENTION

In the light of the circumstances above, an object of the present invention is to provide a simple method for measuring the concentration of OH groups that are contained in trace quantity in quartz glasses of any type, yet at high precision.

Furthermore, another object of the present invention is to provide a method for measuring the concentration of OH groups that are present in the quartz glass at a quantity of less than 1 ppm, yet at a high precision.

To achieve the objects above in accordance with the present invention, there is provided, in measuring the concentration of OH groups contained in quartz glass by means of infrared spectroscopy, a method for measuring the concentration of OH groups that are contained in trace quantity in quartz glass, which comprises preparing a set of test pieces comprising a reference test piece from a blank of a quartz glass body whose OH group content is known and a sample test piece from a quartz glass body whose OH group content is to be measured, whereby the test pieces each have two planar planes faced to each other; setting the sample test piece and the reference test piece in an infrared spectrophotometer; successively irradiating perpendicular to one of the two planar planes an incident infrared radiation in a wavelength region of approximately 2500 nm to approximately 2950 nm, while simultaneously detecting the outgoing radiation spectrum from the other plane; obtaining the difference of the outgoing radiation spectrum of each of the test pieces; selecting the absorbance peak assigned to OH groups at a wavelength of 2720 nm to obtain the peak height thereof; and calculating the concentration of OH groups from the peak height in the sample test piece.

For calculating of the concentration of OH groups that are present in a trace quantity in the sample test piece the following equation is suitable:

$$C_{sample} = C_{blank} + \Delta A / L \times (M_H + M_O) / \varrho \times 10^3 \qquad (2),$$

wherein, $C_{sample}$ represents the concentration (wt·ppm) of OH groups that are present in the sample test piece; $C_{blank}$ represents the concentration (wt·ppm) of OH groups that are present in the reference test piece; $\Delta A$ represents the peak height (ABS.); L represents the length (cm) of optical path; $\epsilon$ represents the absorption coefficient ($1 \cdot mol^{-1} \cdot cm^{-1}$), $M_H$ represents the atomic weight of hydrogen; $M_O$ represents the atomic weight of oxygen; and $\varrho$ represents the density ($g \cdot cm^{-3}$) of quartz glass.

In the measurement method according to the present invention, the baseline inclined by the presence of base absorption can be set horizontally by calculating the concentration of OH groups that are present in a trace quantity in the quartz glass by obtaining the difference spectrum. Furthermore, by selecting the highly sensitive OH groups absorbance peak at the wavelength of 2720 nm, the concentration of OH groups that are present in a trace quantity of lower than 1 ppm can be obtained. Moreover, since the method does not require preparing an optical fiber therefrom, the concentration of OH groups that are present in trace quantity can be measured on any type of quartz glass bodies.

The method according to the present invention requires a quartz glass body to use as a blank whose OH group content is known. However, to measure the concentration of OH groups contained in the sample test piece at high precision, it is preferred to use a blank test peace made from a quartz glass body free from OH groups, i.e., a quartz glass body having an OH content of "0" percent. "A quartz glass body free from OH groups" signifies a quartz glass body whose part is made into a fiber and whose spectrum is measured to confirm that there is no absorption at 1380 nm ascribed to the presence of OH groups. By using this quartz body, the concentration of OH groups that are present in trace quantity can be obtained with high precision.

The precision of measurement can be increased by providing two planes disposed faced to each other and through which the light is passed in such a manner that are placed in parallel with each other and providing them as mirror finished planes, or polished planes or cut planes coated with an oil for matching the refractive index or a reflection preventive agent, such that they yield a center line average roughness $R_a$ of 10 μm or less. A reflection preventive agent is an organic substance free from OH groups and having an effect of reducing the reflection index. Furthermore, an increase in planar precision enables measuring OH group concentration in a further lower range.

The optical path length of the reference test piece and the sample test piece is preferably in a range of from 2 to 50 cm, more preferably, in a range of from 2 to 8 cm. If the length is less than the aforementioned range, it becomes difficult to achieve the required measurement precision, and if the optical path length exceeds 50 cm, the measuring region becomes dark as to make it difficult to make measurements with high precision. In practice, the optical path length is preferably in a length capable of setting it inside the sample chamber of the infrared spectrophotometer, i.e., a length of from about 2 to 8 cm.

If the difference in optical path length for the reference test piece and the sample test piece becomes larger, the inclination of the base line becomes too large as to impair the measurement precision. Accordingly, to perform measurements with high precision, it is effective to decrease the difference in optical path length. Although it is preferred to shorten the difference in optical path length as much as possible, a difference of less than 1% (relating to the optical path length of the reference test piece) makes no problem in practice.

Preferably before setting the sample test piece and the reference test piece in the infrared spectrophotometer, the difference in fictive temperature of the sample test piece and the reference test piece is set to be within 200° C. The difference in fictive temperature between the reference test piece and the sample test piece generates a mismatch between the baseline at the longer wavelength side and the shorter wavelength side. Unlike the case attributed to the difference in optical path or the difference in the planar state, this mismatch leads to a shift of the baseline in the longer wavelength side in parallel with the direction of the longitudinal axis. Accordingly, this mismatch greatly affects the precision of the measurement. The reason for this is presumed to be attributable to the difference in the basic absorbance between the reference test piece and the sample test piece. It is reported in Anand Agarwal, Kenneth M. Davis, Minoru Tomozawa, "A simple IR spectroscopic method for determining fictive temperature of silica glasses", *Journal of Non-Crystalline Solids*, 185 (1995) 191 –198, that the peak position at 1122 $cm^{-1}$ shifts with the change in fictive temperature. The present inventors presume that the peak shift at ca. 3366 $cm^{-1}$ (equivalent to 2970 nm), i.e., the triple overtone of 1122 $cm^{-1}$ according to the reported value in the literature above, shows the change in basic absorbance. According to the understanding above, the peak position shifts to the side of lower wavelength (longer wavelength) with elevating fictive temperature. Thus, when the reference test piece having a lower fictive temperature and the test piece having a higher fictive temperature are measured, it results in an increased baseline at the longer wavelength side, and in a declined baseline in case the fictive temperatures are in the reversed relation. This is confirmed in the measurement performed in the present invention.

To measure with higher precision, it is effective to reduce the difference in the fictive temperatures for the two test pieces. It is preferred that the difference in fictive temperatures is reduced as much as possible. However, a difference in fictive temperatures within 80° C., preferably 50° C., makes no practical problem.

To match the fictive temperature of the reference test piece and that of the sample test piece, the test pieces are each subjected to a heat treatment under the same conditions; otherwise, the fictive temperature of the reference test piece is set to be the same as that of the sample test piece. In particular, the method of subjecting the reference test piece alone to the heat treatment is preferred, because it prevents the fluctuation in the concentration of OH groups from occurring on the sample test piece to be measured.

The fictive temperature is measured by using a Raman spectrophotometer. More specifically, a small piece of a synthetic quartz glass is prepared as a comparative sample; for example, sample 1 obtained by water-quenching a piece once heated at 1200° C. for a duration of 2 hours, sample 2 obtained by water-quenching piece heated at 1000° C. for a duration of 20 hours, sample 3 obtained by water-quenching piece heated at 900° C. for a duration of 120 hours, and sample 4 obtained by water-quenching piece heated at 800° C. for a duration of 1200 hours are prepared, and each of the samples is subjected to Raman spectroscopy in the wavelength range of from 150 to 650 $cm^{-1}$ to obtain the following three peaks:

150 –650 $cm^{-1}$ (W1, peak area AW1);

470–520 $cm^{-1}$ (D1, peak area AD1); and

580–640 $cm^{-1}$ (D2, peak area AD2).

Then, from the three peak areas obtained above, the area ratio I is obtained in accordance with the following equation:

$$I=AD2/(AW1-AD1-AD2) \qquad (3)$$

Then, the relation between the thus obtained value I and the fictive temperature is shown in a graph to provide a standard line (calibration line). Thus, there can be shown a method of obtaining the fictive temperature from its "I" for a sample whose fictive temperature is unknown.

By using the measurement method according to the present invention, the present inventors detected the concentration of OH groups present in trace quantity as low as 0.005 ppm. Presumably, OH groups present at a still lower concentration can be detected by using measurement equipment with higher performance, or by improving the preparation of samples.

DETAILED DESCRIPTION OF THE PREFERRED EMBODIMENTS OF THE INVENTION

Figure 1:
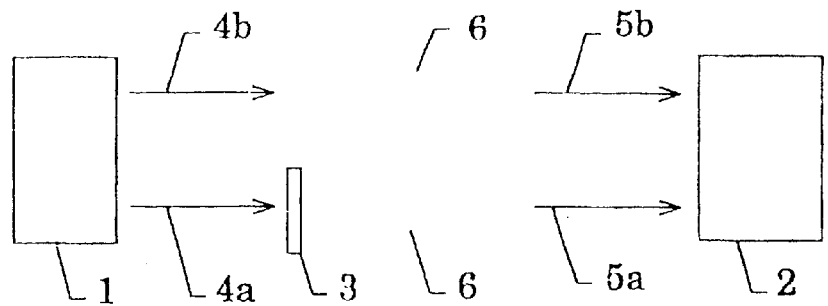
FIG. 1 is a schematic drawing of the adjusting method if an external slit is provided.

The method of measuring the concentration of OH groups by using the measurement method according to the present invention is shown in FIG. 1 to FIG. 4. Referring to FIGS. 1 to 4, the method utilizes a light source 1, a detector 2, an external slit 3, an incident light beam on the side of the sample test piece 4a, an incident light beam on the reference side 4b, a transmitting light beam on the side of the sample test piece 5a, a transmitting light beam on the reference side 5b, a light transmitted through the sample test piece 5c, a light transmitted through the reference test piece 5d, air 6, a sample test piece 7, and a reference test piece 8.

Figure 2:
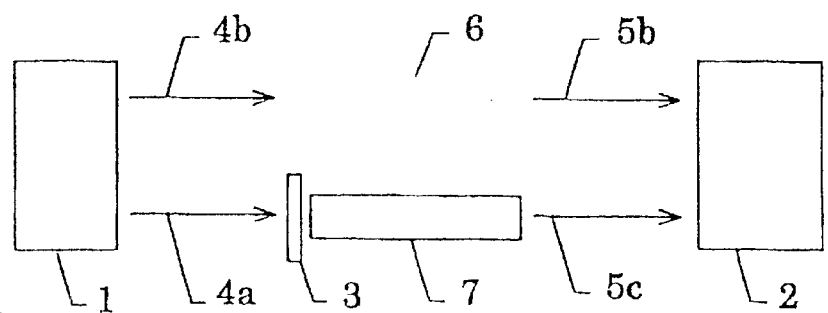
FIG. 2 is a schematic drawing of the measuring method of the measuring test pieces.
Figure 3:
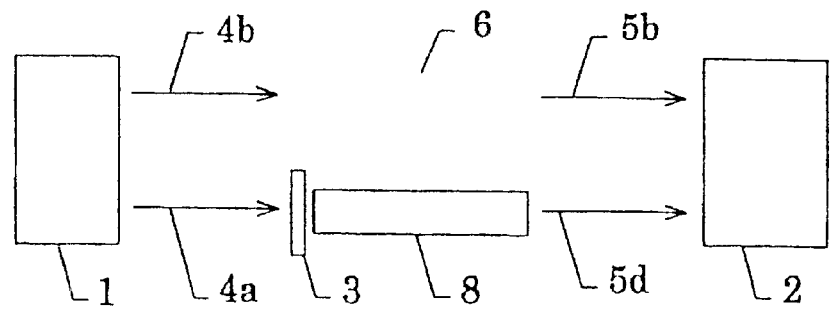
FIG. 3 is a schematic drawing of the measuring method of a reference test piece.
Figure 4:
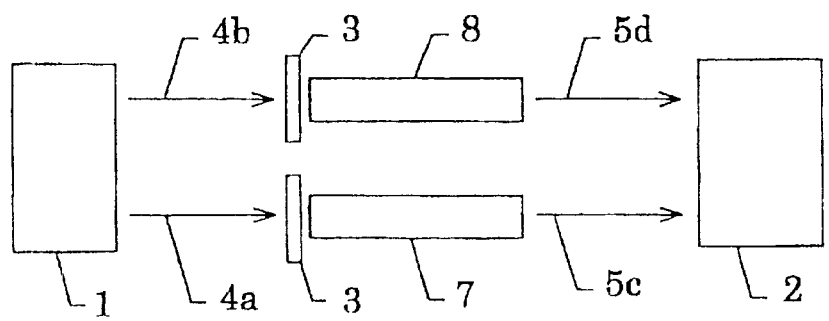
FIG. 4 is a schematic drawing showing the measuring method in which the measuring test piece and the reference test piece are set.

In FIG. 1, an external slit 3 is attached to the sample holder of the infrared spectrophotometer. After attaching the external slit, for instance, the alignment is preferably made in a manner so that a visible light (for instance, a visible light 500 nm in wavelength) is irradiated from the light source 1, and that the light might pass through the center of the hole of the external slit 3. With the external slit being attached, zero adjustment is made by irradiating a measuring light having a wavelength in the range of from 2500 to 2950 nm. Then, the sample test piece 7 is set in front of the external slit in such a manner that the incident light might make a right angle, and a measuring light having a wavelength in a range of from 2500 to 2950 nm is irradiated thereto to detect the spectrum of the transmitted light (FIG. 2). Similarly, the reference test piece 8 is also set in front of the external slit in such a manner that it might make a right angle with the incident light beam, and the spectrum of the transmitted light is detected by irradiating a measuring light having a wavelength in a range of from 2500 to 2950 nm (FIG. 3). A spectrum of the transmitted light beam thus obtained is converted into absorbance, and the difference spectrum is obtained therefrom. From the resulting difference spectrum, the peak height at a wavelength of 2720 nm is substituted in equation (2) to calculate the concentration of the OH groups. As the absorption coefficient, there can be used, for instance, the value of 77.5 ($1 \cdot mol^{-1} \cdot cm^{-1}$), which is reported in G. Hetherington and K. H. Jack, "Water in vitreous silica Part I., Influence of 'water' content on the properties of vitreous silica", *Phys. Chem. Glasses* 3 (1962) 129. To obtain the difference spectrum, there can be mentioned a method comprising measuring the transmittance of the test specimen to be measured and that of the blank test specimen while using air as the reference and setting it as 0, and obtaining the difference spectrum thereof; or, as shown in FIG. 4, after setting the test piece 7 in front of the external slit in such a manner that it should make a right angle with respect to the incident light beam, setting a reference test piece 8 on the reference side in front of the external slit having the same shape as that above in such a manner that it should make a right angle with respect to the incident light beam, and irradiating a measuring light in the wavelength range of from 2500 to 2950 nm to detect each of the spectra of the transmitted light beams to obtain the difference spectrum from the thus obtained transmitted light beams.

The present invention is explained in detail based on the examples, but it should be noted that the present invention is not limited thereto.

EXAMPLE 1

As a reference test piece, a soot body free of Germanium was prepared by VAD method, i.e., a method used for the preparation of optical fiber preforms, and after cutting out a test piece from the dehydrated and sintered quartz glass body, the two planes through which the light is transmitted were mirror polished using cerium oxide to obtain a test piece (1 cm in square side and 4 cm in length) having an optical path length of 4 cm. Separately, a fiber was prepared by using the quartz glass body as the core and depositing a clad portion containing fluorine thereon, and was confirmed on its wavelength spectrum that it showed no OH absorption at the wavelength of 1380 nm.

As a sample test piece, a quartz glass body "A" was obtained by treating a soot body prepared in the same production process as above in such a manner that the dehydrated product thereof contained halogen compounds at a concentration accounting for about 90% of the aforementioned specimen, followed by sintering and cutting out the test pieces. Similarly, quartz glass bodies "B" and "C" were prepared in the same manner, but the dehydrated products contained halogen compounds at a concentration of about 60% and 50%, respectively. (The test pieces thus obtained are referred to hereinafter as test pieces A, B, and C, respectively.)

Measurement of fictive temperature was performed on each of the reference test piece and the sample test pieces to be measured thus prepared, and the fictive temperatures were found to be 1400° C. and 1100° C., respectively. Thus, to match the fictive temperatures, the reference test piece was heated at 1100° C. for a period of 30 hours and water-quenched. Measurement of the fictive temperature was performed again to obtain 1100° C. Thus, the fictive temperature of the reference test piece was matched to that of the sample test piece.

The two light transmitting planar planes of the quartz glass bodies of the reference test piece and the sample test pieces A, B, and C were each mirror polished using cerium oxide to obtain sample test pieces each having a square side of 1 cm and a length of 4 cm and each having an optical path length of 4 cm.

The sample test pieces and the reference test piece above each having an optical path length of 4 cm were each set in an ultraviolet visible near infrared spectrophotometer (Trade name: λ-900, manufactured by Perkin-Elmer Inc.) while using air as the reference, and the transmittance for a measuring light having a wavelength in the range of from 2500 to 2950 nm was detected in accordance with the process steps shown in FIGS. 1 to 3 as follows.

First, the peak height of the absorbance obtained from the absorbance curve of the difference spectra of each of the test pieces was substituted in equation (2) to obtain the concentration of the OH groups by using the absorption coefficient of 77.5 ($1 \cdot mol^{-1} \cdot cm^{-1}$), which results are given in Table 1. The absorbance curve of the difference spectrum for sample test piece A is shown in FIG. 5.

Figure 5:
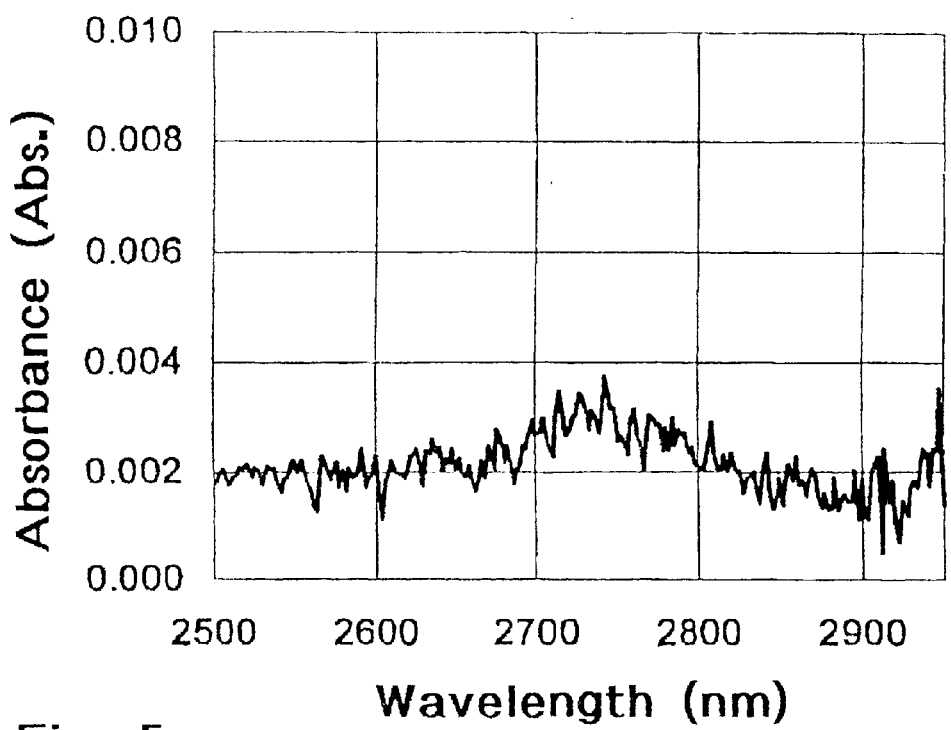
FIG. 5 is an absorbance curve based on a difference spectrum obtained for a measuring test piece containing 0.025 ppm of OH groups, if there is no difference in a fictive temperature and optical path length between the measuring test piece and the reference test piece, and in which the test pieces are provided with mirror polished light transmitting two planes.

Referring to FIG. 5, tilting attributed to the base absorption is not observed in the base line. The measured results for sample test pieces A, B, and C are 0.025 ppm, 0.20 ppm, and 0.5 ppm, respectively, and the precision of the measurement after repeated measurements was also found to be fair. Hence, the measured results can be treated as the true values.

EXAMPLE 2

A measurement was performed in the same manner as in Example 1 above, except for using a sample test piece prepared by mirror polishing using cerium oxide in such a manner that the optical path length should be longer by 10% than that of the reference test piece.

Figure 6:
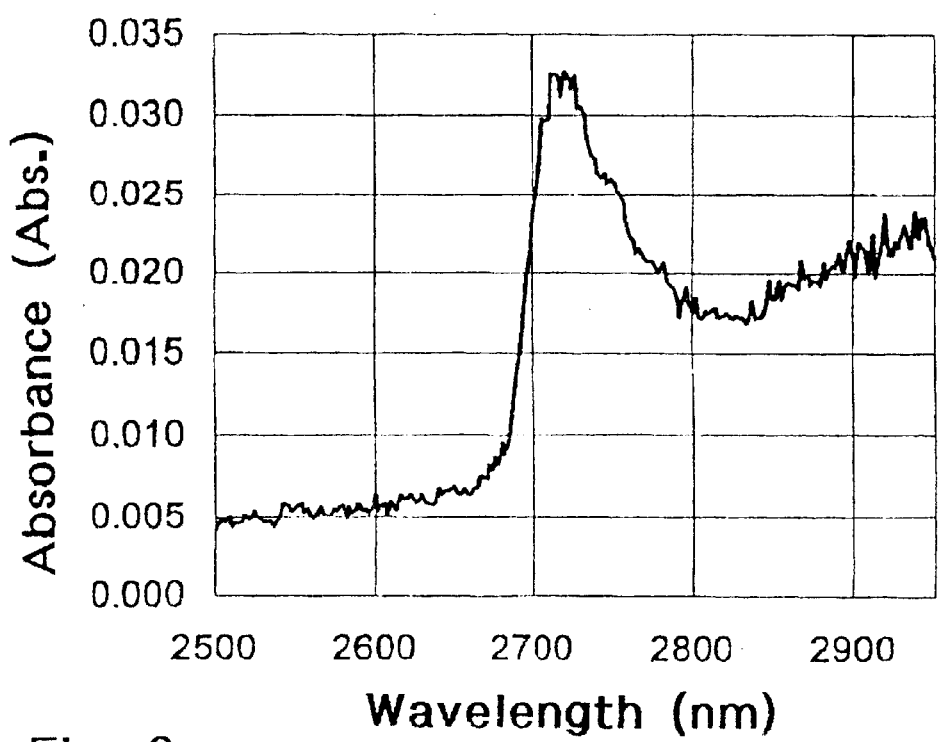
FIG. 6 is an absorbance curve based on a difference spectrum obtained for a measuring test piece containing 0.5 ppm of OH groups, if the optical path length of the measuring test piece is longer than that of the reference test piece by 10%, meanwhile there is no difference of fictive temperature between them, and in which the test pieces are provided with mirror polished light transmitting two planes.

The concentration of the OH groups obtained from the absorbance curve of the difference spectrum is shown in Table 1. Furthermore, the absorbance curve of the difference spectrum using the sample test piece C is shown in FIG. 6. The measured results for test pieces A, B, and C were "–", 0.18 ppm, and 0.5 ppm, respectively. It was found impossible to perform the measurement for the sample test piece A. A slight deviation from the result (true value) obtained in Example 1 was observed on sample test piece B. Under the present measuring conditions, the concentration of OH groups that are present in trace quantity could be obtained as low as 0.5 ppm with high precision.

EXAMPLE 3

Measurements were performed in the same manner as in Example 1 above, except for using a sample test piece and a reference test piece each prepared by polishing the light transmitting two planes using #1200 abrasive.

Figure 7:
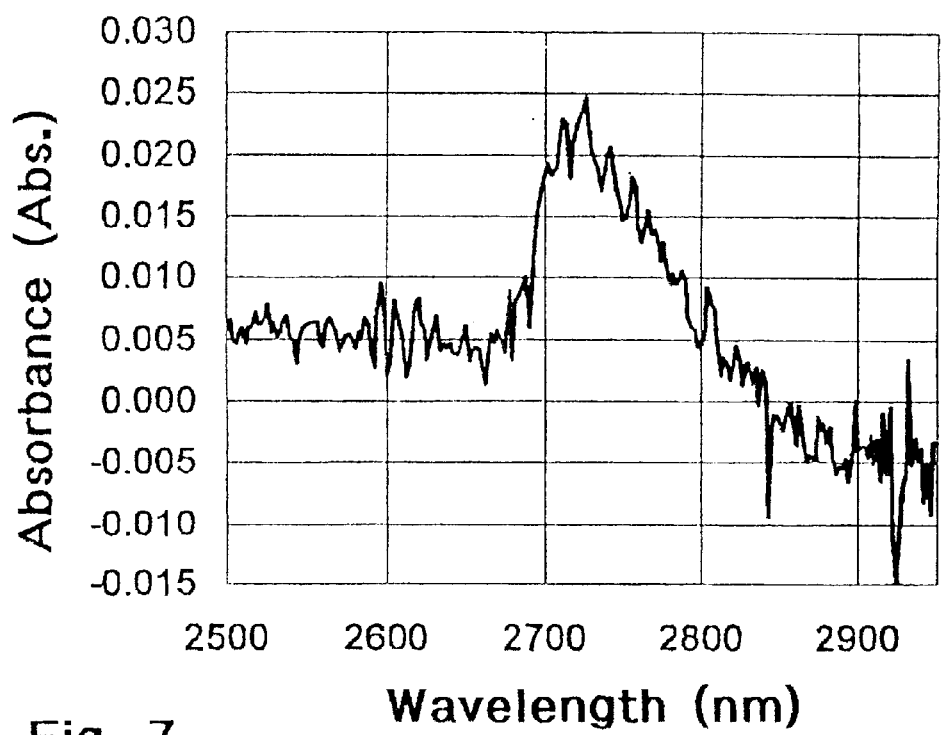
FIG. 7 is an absorbance curve based on a difference spectrum obtained for a measuring test piece containing 0.5 ppm of OH groups, if there is no difference in a fictive temperature and optical path length between the measuring test piece and the reference test piece, and in which the test pieces are provided with light transmitting two planes polished by using #1200 abrasive.

The concentration of the OH groups obtained from the absorbance curve of the difference spectrum is shown in Table 1. Furthermore, the absorbance curve of the difference spectrum using the sample test piece C is shown in FIG. 7. The measured results for sample test pieces A, B, and C were "–", 0.18 ppm, and 0.5 ppm, respectively. It was found impossible to perform the measurement for the sample test piece A. For the sample test piece B, a slight difference was observed from the result (true value) obtained in Example 1. Under the present measuring conditions, the concentration of OH groups that are present in trace quantity could be obtained as low as 0.5 ppm with high precision.

EXAMPLE 4

A measurement was performed in the same manner as in Example 1 above, except for using a measuring test piece and a reference test piece each prepared by polishing the light transmitting two planes using #1200 abrasive, and by then coating the polished planes with Paraffin liquid for spectroscopy Uvasol, manufactured by MERCK Inc.

Figure 8:
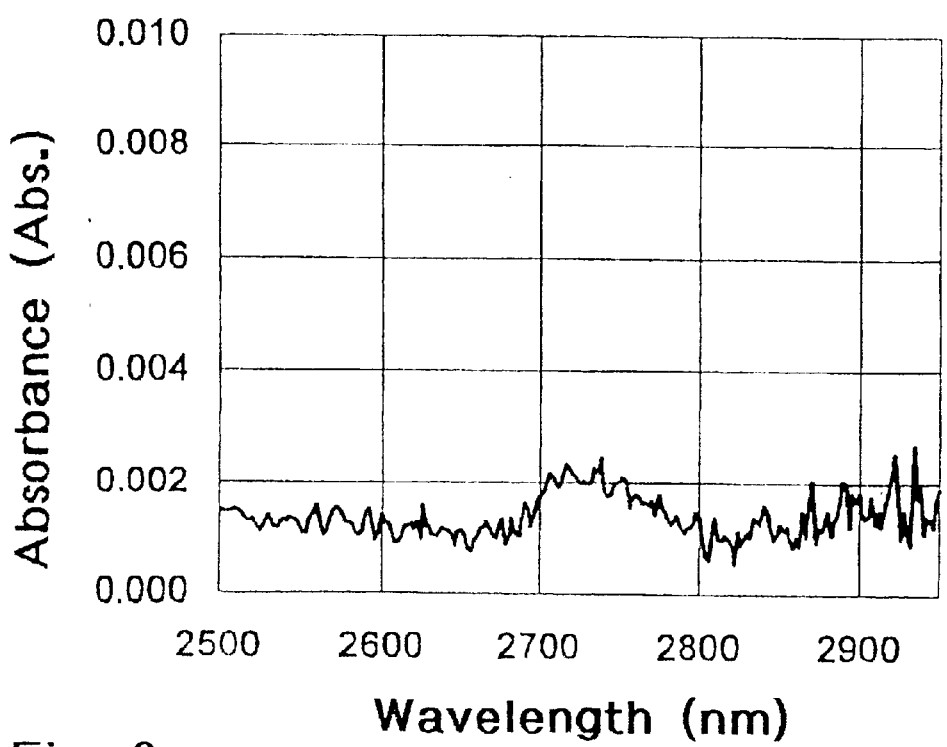
FIG. 8 is an absorbance curve based on a difference spectrum obtained for a measuring test piece containing 0.025 ppm of OH groups, if there is no difference in a fictive temperature and optical path length between the measuring test piece and the reference test piece, and in which the test pieces are provided with light transmitting two planes polished by using #1200 abrasive and then coated with Paraffin liquid for spectroscopy Uvasol, manufactured by MERCK Inc.

The concentration of the OH groups obtained from the absorbance curve of the difference spectrum is shown in Table 1. Furthermore, the absorbance curve of the difference spectrum using the sample test piece A is shown in FIG. 8. The measured results for sample test pieces A, B, and C were 0.025 ppm, 0.20 ppm, and 0.5 ppm, respectively. Under the present measuring conditions, the concentration of OH groups that are present in trace quantity could be obtained as low as 0.025 ppm with high precision.

Comparative Example 1

Figure 9:
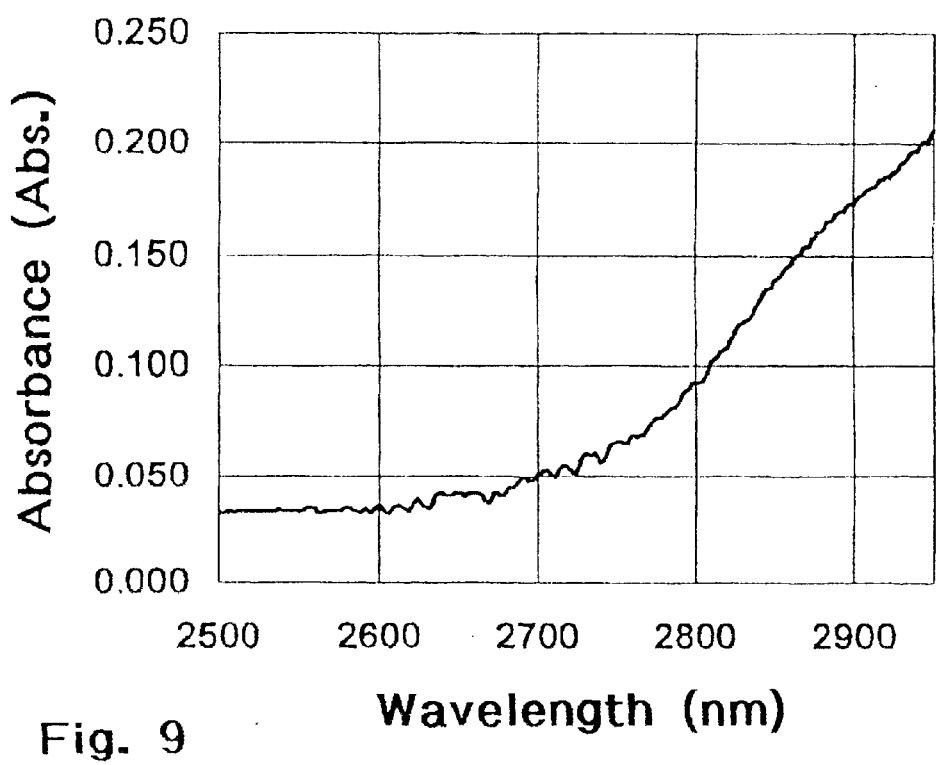
FIG. 9 is an absorbance curve obtained by a conventional method for a measuring test piece containing 0.025 ppm of OH groups.

For the measuring sample test pieces used in Example 1, attempts were made to obtain the peak height in absorbance from the absorbance curve obtained by performing the measurements in a manner similar to the conventional method using air as the reference. For the sample test pieces A and B, however, it was found that the tilting of the baseline by the base absorbance was too large to distinguish the peaks. For the sample test piece C, the measured result was found to be greatly deviated from the result (true value) obtained in Example 1. The absorbance curve for sample test piece A is shown in FIG. 9.

Comparative Example 2

The sample test pieces used in Example 1 were subjected to measurements similar to that described in Example 1, except that the fictive temperature was matched previously. The concentration of the OH groups obtained from the absorbance curve of the difference spectrum is shown in Table 1.

Figure 10:
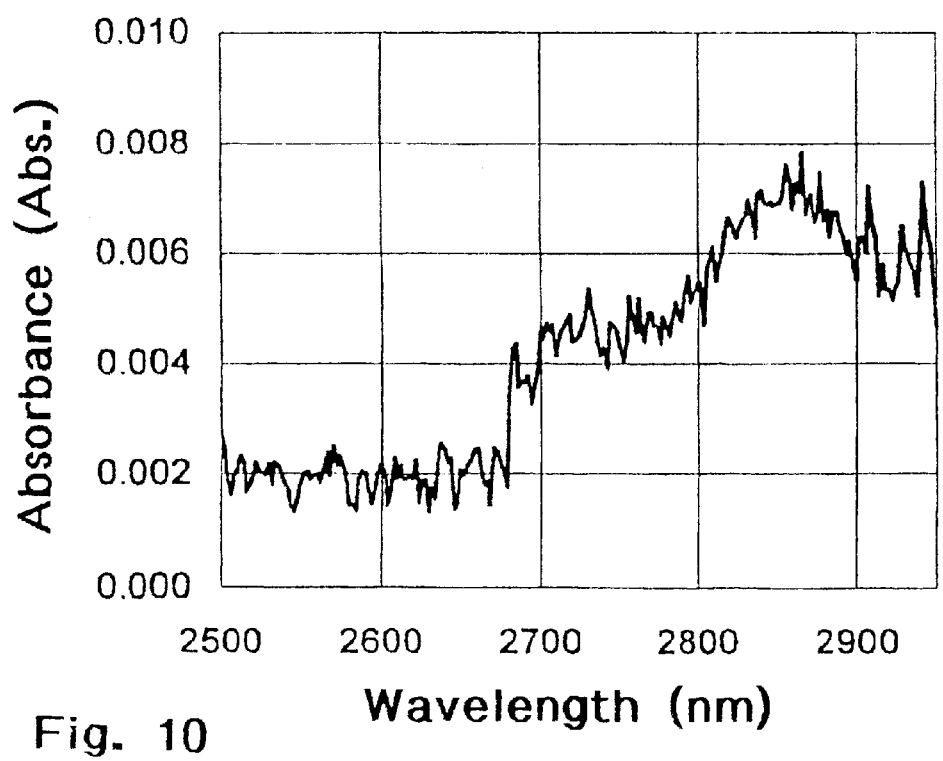
FIG. 10 is an absorbance curve based on difference spectrum obtained for a measuring test piece containing 0.025 ppm of OH groups, in case there is no difference in optical path length between the measuring test piece and the reference test piece, and in which the test piece has a fictive temperature lower than that of the reference test piece by 300° C.

The measured results for sample test pieces A, B, and C were "–", 0.20 ppm, and 0.5 ppm, respectively, but for sample test piece A, it was found impossible to perform the measurement as compared with the results obtained in Example 1. As can be read from FIG. 10, this is attributed to the fact that the peak could not be distinguished due to the mismatch in base line attributed to the difference in fictive temperatures.

All of the measuring and reference test pieces used in Examples 1 to 4 as well as in Comparative Example 1 and 2 were subjected to mirror polishing again by using cerium oxide in such a manner that the optical path length may become 3.8 cm, and measurements were performed thereon in a manner similar to that described in Example 1. As a result, the concentration values of OH groups for all of the measured test specimens were found to be in good agreement of the measured values obtained in Example 1. Accordingly, it can be understood that the deviation in measured results as read in Table 1 is attributed to the difference in measuring methods, and not to the difference in concentration of the OH groups contained in the test pieces.

TABLE 1

| | Δ(Tf) (° C.) | l₀ (mm) | Δ(l₀) (%) | Plane quality | Result of measured OH group conc. (wt.-ppm) | | |
| --- | --- | --- | --- | --- | --- | --- | --- |
| | | | | | Test piece A | Test piece B | Test piece C |
| Ex. 1 | 0 | 40 | 0 | Mirror | 0.025 | 0.20 | 0.5 |
| Ex. 2 | 0 | 44 | 10 | Mirror | — | 0.18 | 0.5 |
| Ex. 3 | 0 | 40 | 0 | Polished | — | 0.18 | 0.5 |
| Ex. 4 | 0 | 40 | 0 | Paraffin coated | 0.025 | 0.20 | 0.5 |
| Comp. Ex. 1 | — | 40 | — | Mirror | — | — | 0.4 |
| Comp. Ex. 2 | 300 | 40 | 0 | Mirror | — | 0.20 | 0.5 |

Δ(Tf) = difference in fictive temperature;
l₀ optical path length;
Δ(l₀) = difference in optical path length From Table 1 above, it can be seen that the base absorption observed in the base line can be eliminated by the method of analysis according to the present invention, and that the concentration of OH groups that are present in trace quantity in quartz glass can be measured with high precision without preparing fibers therefrom.

The measuring method according to the present invention enables the determination of the concentration of OH groups with high precision that are present in trace quantities of less than 1 wt.-ppm in any type of quartz glass bodies without preparing fibers therefrom.

What is claimed is:

1. A method for measuring the concentration of OH groups that are contained in trace quantity in quartz glass, which comprises preparing a set of test pieces comprising a reference test piece from a blank of a quartz glass body whose OH group content is known and a sample test piece from a quartz glass body whose OH group content is to be measured, whereby the test pieces each have two planar planes faced to each other; setting the sample test piece and the reference test piece in an infrared spectrophotometer; successively irradiating perpendicular to one of the two planar planes an incident infrared radiation in a wavelength region of approximately 2500 nm to approximately 2950 nm, while simultaneously detecting the outgoing radiation spectrum from the other plane; obtaining the difference of the outgoing radiation spectrum of each of the test pieces; selecting the absorbance peak assigned to OH groups at a wavelength of 2720 nm to obtain the peak height thereof; and calculating the concentration of OH groups from the peak height in the sample test piece.

2. A method as claimed in claim 1, wherein the concentration of OH groups in the sample test piece is calculated in accordance with the following equation:

$$C_{sample} = C_{blank} + \Delta A/L\epsilon \times (M_H + M_O)/\varrho \times 10^3 \text{ wherein,}$$

$C_{sample}$ represents the concentration (wt·ppm) of OH groups that are present in the sample test piece; $C_{blank}$ represents the concentration (wt·ppm) of OH groups that are present in the reference test piece; $\Delta A$ represents the peak height (ABS.); L represents the length (cm) of optical path; $\epsilon$ represents the absorption coefficient (1·mol⁻¹·cm⁻¹), $M_H$ represents the atomic weight of hydrogen; $M_O$ represents the atomic weight of oxygen; and $\varrho$ represents the density (g·cm⁻³) of quartz glass).

3. A method as claimed in claim 1, wherein a quartz glass body free from OH groups is used as the blank quartz body.

4. A method as claimed in claim 1, wherein the two planar planes each of the sample test piece and the reference test piece, are placed in the infrared spectrophotometer in parallel with each other and the planar planes are mirror polished planes, or polished planes or cut planes coated with an oil for matching the refractive index or a reflection preventive agent, having a center line average roughness $R_a$ of 10 μm or less.

5. A method as claimed in claim 1, wherein the length of the optical path of the sample test piece and the reference test piece is in a range of from 2 to 50 cm.

6. A method as claimed in claim 5, wherein the length of the optical path is in a range of from 2 to 8 cm.

7. A method as claimed in claim 6, wherein the difference in length of the optical path of the sample test piece and the reference test piece is within 1% of the length of the reference test piece.

8. A method as claimed in claim 1, wherein the difference in length of the optical path of the sample test piece and the reference test piece is within 1% of the length of the reference test piece.

9. A method as claimed in claim 1, wherein the difference in fictive temperature of the sample test piece and of the reference test piece is within 200° C.

10. A method as claimed in claim 9, wherein the difference in fictive temperature of the two test pieces is within 80° C.

11. A method as claimed in claim 9, wherein the difference in fictive temperature of the two test pieces is within 50° C.

* * * * *